(12) United States Patent
Marczyk et al.

(10) Patent No.: US 8,231,041 B2
(45) Date of Patent: Jul. 31, 2012

(54) VARIABLE COMPRESSION SURGICAL FASTENER CARTRIDGE

(75) Inventors: Stanislaw Marczyk, Stratford, CT (US); John W. Beardsley, Hamden, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 301 days.

(21) Appl. No.: 12/417,696

(22) Filed: Apr. 3, 2009

(65) Prior Publication Data

US 2009/0255976 A1    Oct. 15, 2009

Related U.S. Application Data

(60) Provisional application No. 61/044,652, filed on Apr. 14, 2008.

(51) Int. Cl.
  *A61B 17/04* (2006.01)
  *A61B 17/10* (2006.01)
(52) U.S. Cl. .................. 227/178.1; 227/177.1
(58) Field of Classification Search .............. 227/178.1, 227/175.1–182.1; 606/142–143, 219–221
See application file for complete search history.

(56) References Cited

U.S. PATENT DOCUMENTS

| | | |
|---|---|---|
| 1,756,670 A | 4/1930 | Treat |
| 3,258,012 A | 6/1966 | Nakayama et al. |
| 3,744,495 A | 7/1973 | Johnson |
| 3,771,526 A | 11/1973 | Rudie |
| 3,837,555 A | 9/1974 | Green |
| 4,014,492 A | 3/1977 | Rothfuss |
| 4,278,091 A | 7/1981 | Borzone |
| 4,319,576 A | 3/1982 | Rothfuss |
| 4,527,437 A | 7/1985 | Wells |
| 4,531,522 A | 7/1985 | Bedi et al. |
| 4,532,927 A | 8/1985 | Miksza, Jr. |
| 4,548,202 A | 10/1985 | Duncan |
| 4,573,469 A | 3/1986 | Golden et al. |
| 4,605,001 A | 8/1986 | Rothfuss et al. |

(Continued)

FOREIGN PATENT DOCUMENTS

EP    0 129 442    12/1984

(Continued)

OTHER PUBLICATIONS

European Search Report mailed Oct. 19, 2009 in EP Application No. 09251240.9 filed May 1, 2009.

(Continued)

*Primary Examiner* — Rinaldi I Rada
*Assistant Examiner* — Robert Long

(57) ABSTRACT

A surgical fastener applying apparatus comprising a cartridge body including a tissue contacting surface including a plurality of fastener retention slots arranged in a plurality of rows including at least an inner row and an outer row, a plurality of surgical fasteners disposed in the inner and outer rows and configured such that a plurality of fasteners disposed in the inner row have a first diameter that is less than a second diameter of a plurality of surgical fasteners disposed in the outer row, and an anvil having an inner row and an outer row of depressions for forming the fasteners. A plurality of pushers are operably associated with the plurality of surgical fasteners, the pushers configured to eject an associated surgical fastener towards the respective depression in the anvil such that upon formation of a corresponding surgical fastener, the surgical fasteners ejected from the inner row provide a greater compressive force to tissue than the surgical fasteners ejected from the outer row.

19 Claims, 9 Drawing Sheets

U.S. PATENT DOCUMENTS

| | | | |
|---|---|---|---|
| 4,608,981 A | 9/1986 | Rothfuss et al. |
| 4,610,383 A | 9/1986 | Rothfuss et al. |
| 4,627,437 A | 12/1986 | Bedi et al. |
| 4,741,336 A | 5/1988 | Failla et al. |
| 4,767,044 A | 8/1988 | Green |
| 4,809,695 A | 3/1989 | Gwathmey et al. |
| 4,848,637 A | 7/1989 | Pruitt |
| 4,881,545 A | 11/1989 | Isaacs et al. |
| 4,930,503 A | 6/1990 | Pruitt |
| 4,941,623 A | 7/1990 | Pruitt |
| 4,978,049 A | 12/1990 | Green |
| 5,027,834 A | 7/1991 | Pruitt |
| 5,108,422 A | 4/1992 | Green et al. |
| 5,180,092 A | 1/1993 | Crainich |
| 5,201,746 A | 4/1993 | Shichman |
| 5,209,756 A | 5/1993 | Seedhom et al. |
| 5,219,353 A | 6/1993 | Garvey, III et al. |
| 5,240,163 A | 8/1993 | Stein et al. |
| 5,282,829 A | 2/1994 | Hermes |
| 5,342,396 A | 8/1994 | Cook |
| 5,350,400 A | 9/1994 | Esposito et al. |
| 5,352,229 A | 10/1994 | Goble et al. |
| 5,425,489 A | 6/1995 | Shichman et al. |
| 5,439,479 A | 8/1995 | Shichman et al. |
| 5,452,836 A | 9/1995 | Huitema et al. |
| 5,452,837 A | 9/1995 | Williamson, IV et al. |
| 5,470,010 A | 11/1995 | Rothfuss et al. |
| 5,484,095 A | 1/1996 | Green et al. |
| 5,497,931 A | 3/1996 | Nakamura |
| 5,501,693 A | 3/1996 | Gravener |
| 5,509,920 A | 4/1996 | Phillips et al. |
| 5,571,116 A | 11/1996 | Bolanos |
| 5,571,285 A | 11/1996 | Chow et al. |
| 5,584,856 A | 12/1996 | Jameel et al. |
| 5,620,452 A | 4/1997 | Yoon |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos et al. |
| 5,697,542 A | 12/1997 | Knodel et al. |
| 5,709,680 A | 1/1998 | Yates et al. |
| 5,741,268 A | 4/1998 | Schutz |
| 5,810,822 A | 9/1998 | Mortier |
| 5,865,361 A | 2/1999 | Milliman et al. |
| 5,871,135 A | 2/1999 | Williamson, IV et al. |
| 5,879,371 A | 3/1999 | Gardiner et al. |
| 5,915,616 A | 6/1999 | Viola et al. |
| 5,961,521 A | 10/1999 | Roger |
| 5,964,394 A | 10/1999 | Robertson |
| 6,083,242 A | 7/2000 | Cook |
| 6,202,914 B1 | 3/2001 | Geiste et al. |
| 6,273,897 B1 | 8/2001 | Dalessandro et al. |
| 6,325,810 B1 | 12/2001 | Hamilton et al. |
| 6,348,054 B1 | 2/2002 | Allen |
| 6,702,826 B2 | 3/2004 | Liddicoat et al. |
| 6,706,057 B1 | 3/2004 | Bidoia et al. |
| 6,786,382 B1 | 9/2004 | Hoffman |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,001,411 B1 | 2/2006 | Dean |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,377,928 B2 | 5/2008 | Zubik et al. |
| 7,398,908 B2 | 7/2008 | Holsten et al. |
| 7,407,076 B2 | 8/2008 | Racenet et al. |
| 7,455,676 B2 | 11/2008 | Holsten et al. |
| 7,500,979 B2 | 3/2009 | Hueil et al. |
| 7,604,151 B2 * | 10/2009 | Hess et al. ............... 227/181.1 |
| 7,641,091 B2 | 1/2010 | Olson et al. |
| 7,794,475 B2 | 9/2010 | Hess et al. |
| 2002/0042621 A1 | 4/2002 | Liddicoat et al. |
| 2004/0004105 A1 | 1/2004 | Jankowski |
| 2004/0073222 A1 | 4/2004 | Koseki |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales |
| 2005/0023324 A1 | 2/2005 | Doll et al. |
| 2005/0023325 A1 | 2/2005 | Gresham et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummins |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ringl |
| 2006/0049230 A1 | 3/2006 | Shelton, IV et al. |
| 2006/0085030 A1 | 4/2006 | Bettuchi et al. |
| 2006/0097026 A1 | 5/2006 | Shelton, IV |
| 2006/0124688 A1 | 6/2006 | Racenet et al. |
| 2006/0163312 A1 | 7/2006 | Viola et al. |
| 2006/0226196 A1 | 10/2006 | Hueil et al. |
| 2007/0010838 A1 | 1/2007 | Shelton, IV et al. |
| 2007/0131732 A1 | 6/2007 | Holsten et al. |
| 2007/0262116 A1 | 11/2007 | Hueil et al. |
| 2008/0078800 A1 | 4/2008 | Hess et al. |
| 2008/0078804 A1 | 4/2008 | Shelton et al. |
| 2008/0172088 A1 * | 7/2008 | Smith et al. ................. 606/219 |
| 2009/0112233 A1 * | 4/2009 | Xiao ............................ 606/143 |
| 2009/0255974 A1 * | 10/2009 | Viola ......................... 227/176.1 |
| 2009/0255975 A1 * | 10/2009 | Zemlok et al. ............. 227/178.1 |
| 2009/0255976 A1 * | 10/2009 | Marczyk et al. ........... 227/178.1 |
| 2009/0255977 A1 * | 10/2009 | Zemlok ....................... 227/178.1 |
| 2009/0277946 A1 * | 11/2009 | Marczyk .................... 227/176.1 |
| 2009/0277948 A1 * | 11/2009 | Beardsley et al. .......... 227/178.1 |
| 2011/0101067 A1 * | 5/2011 | Johnson et al. ............ 227/176.1 |
| 2011/0168760 A1 * | 7/2011 | Viola et al. ................. 227/180.1 |
| 2011/0315739 A1 * | 12/2011 | Sniffin et al. ............... 227/176.1 |
| 2012/0046692 A1 * | 2/2012 | Smith et al. .................. 606/219 |

FOREIGN PATENT DOCUMENTS

| | | |
|---|---|---|
| EP | 0 169 044 | 1/1986 |
| EP | 0588081 | 3/1994 |
| EP | 0588081 A | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1 607 048 A1 | 12/2005 |
| EP | 1607048 | 12/2005 |
| EP | 1728473 | 12/2006 |
| EP | 1728473 A | 12/2006 |
| EP | 1 754 445 A2 | 2/2007 |
| EP | 1 875 868 | 1/2008 |
| EP | 2 095 777 | 9/2009 |
| FR | 2838952 | 10/2003 |
| GB | 2 019 296 | 10/1979 |
| GB | 2019296 A | 10/1979 |
| GB | 2 051 287 | 3/1980 |
| GB | 2029754 A | 3/1980 |
| GB | 2 051 287 | 1/1981 |
| GB | 2051287 A | 1/1981 |
| SU | 405234 | 9/1975 |
| SU | 1333319 | 8/1987 |

| | | |
|---|---|---|
| SU | 1442191 | 12/1988 |
| SU | 1459659 | 2/1989 |
| WO | WO 86/02254 A1 | 4/1986 |
| WO | WO 90/05489 | 5/1990 |
| WO | WO 96/19146 | 6/1996 |
| WO | WO 97/34533 | 9/1997 |
| WO | WO02/30296 | 4/2002 |
| WO | WO 02/30296 A | 4/2002 |
| WO | WO 03/094743 | 11/2003 |
| WO | WO 03/094747 | 11/2003 |
| WO | WO2006/055385 | 5/2006 |
| WO | WO 2006/055385 A | 5/2006 |
| WO | WO 2008/007377 | 1/2008 |
| WO | WO2008/089050 | 7/2008 |

OTHER PUBLICATIONS

European Examination Report mailed Sep. 20, 2010 in European Patent Application No. EP 09 251 793.7.

European Search Report mailed Nov. 16, 2009 in European Patent Application No. EP 09 251 793.7, filed Jul. 15, 2009.

European Search Report for EP 06016963.8-2318 date of completion is Mar. 9, 2007.

International Search Report from EP Application No. 07 25 4366 dated Nov. 11, 2010.

International Search Report from EP Application No. 09 25 1067 mailed Mar. 17, 2011.

European Search Report EP08 25 2283 dated Jan. 15, 2009.

European Search Report EP09 25 1224.3-2310 dated Oct. 8, 2009.

European Search Report EP09 251793.7 dated Nov. 16, 2009.

European Search Report EP11004299.1269 dated Aug. 12, 2011.

European Search Report EP9251240.9 dated Oct. 19, 2009.

* cited by examiner

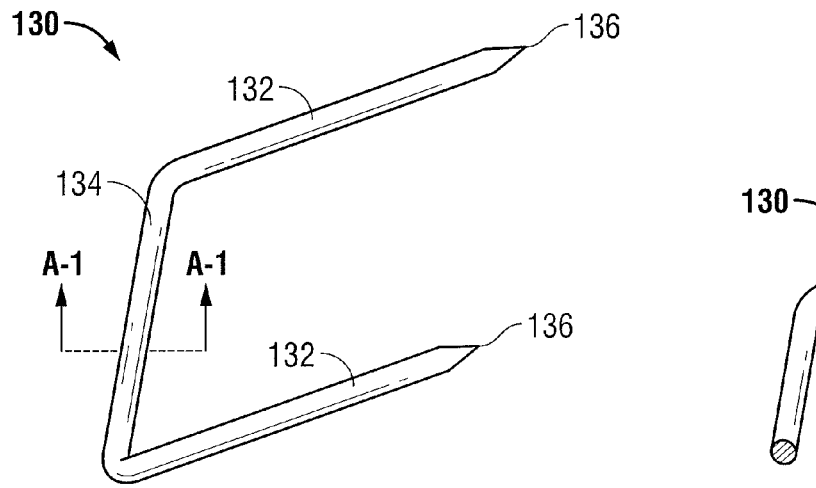
FIG. 5A　　FIG. 5A-1
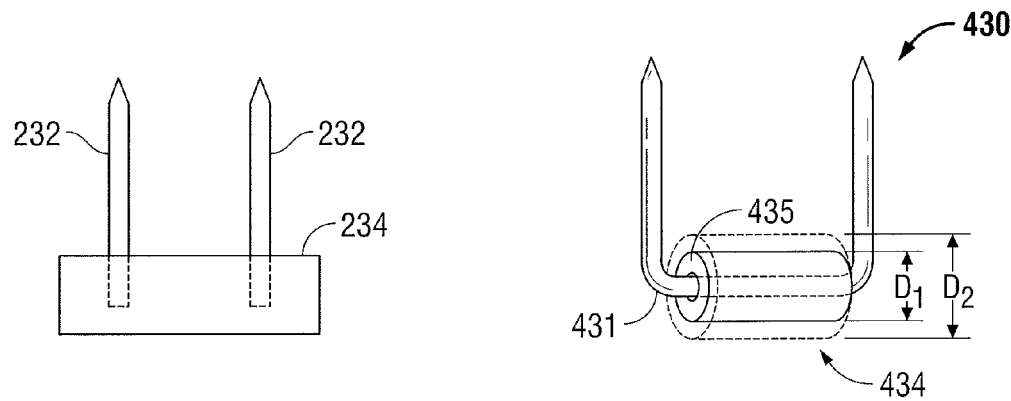
FIG. 6A　　FIG. 6B
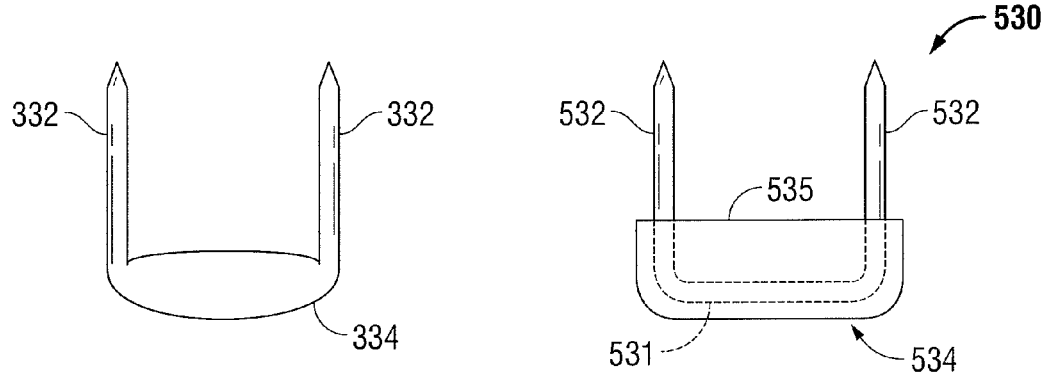
FIG. 6C　　FIG. 6D

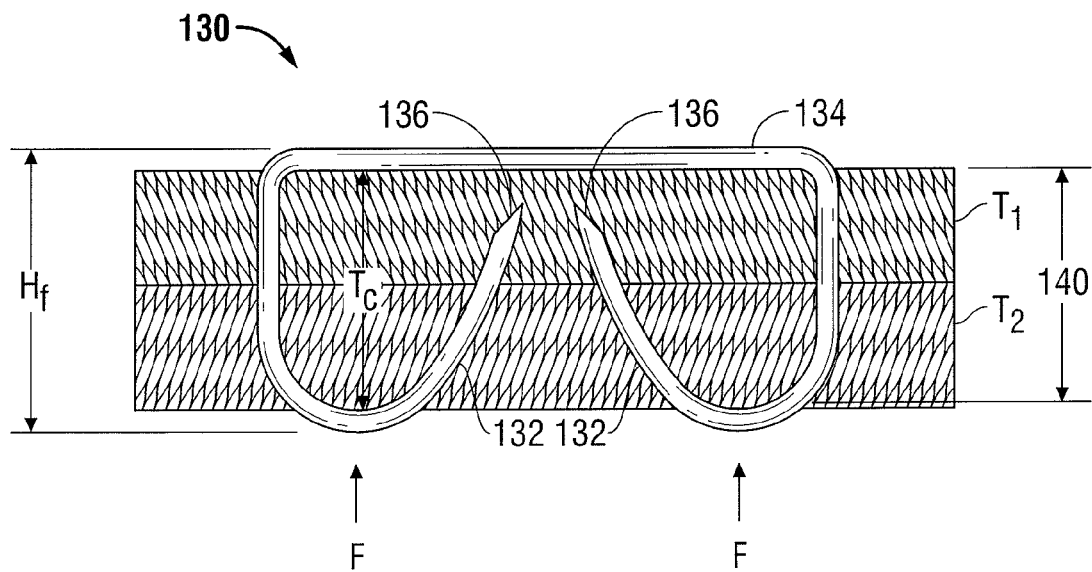
FIG. 7
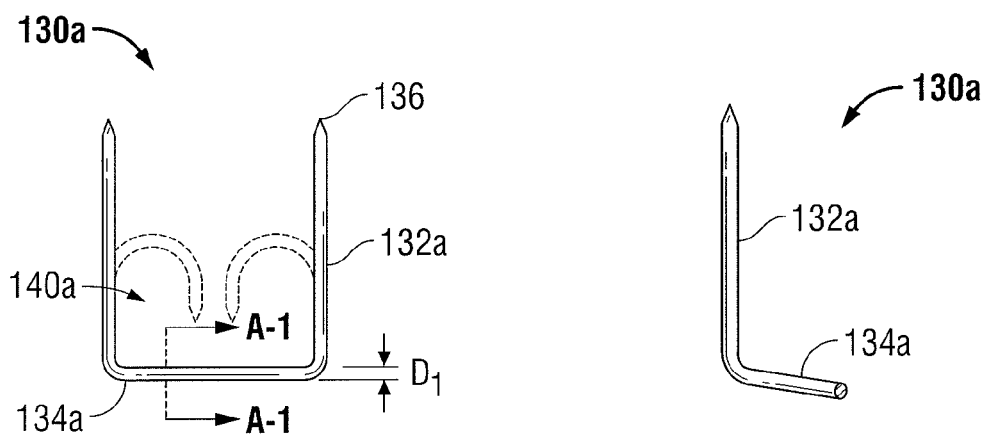
FIG. 8A  FIG. 8A-1

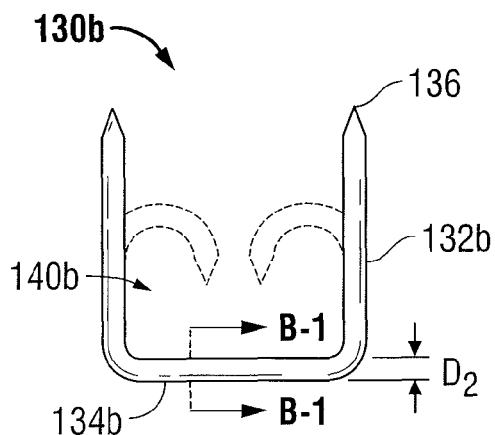 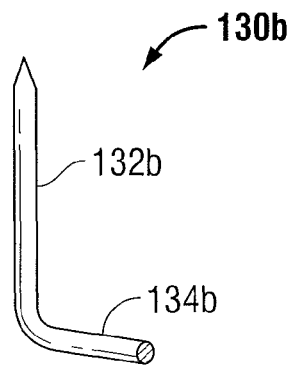
FIG. 8B          FIG. 8B-1
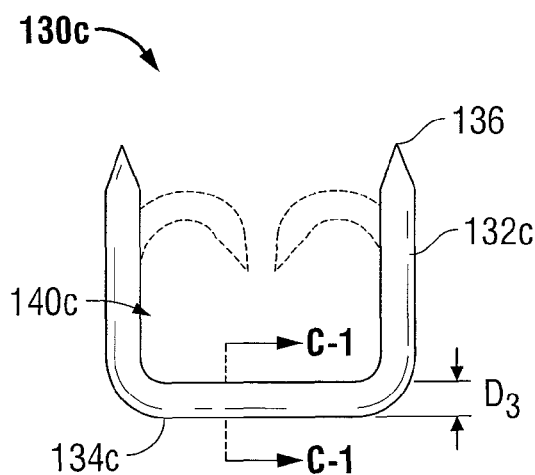 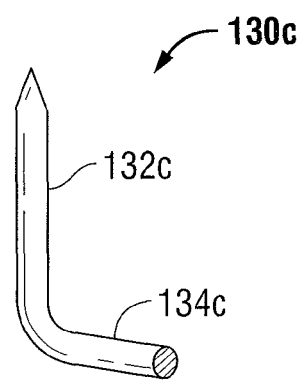
FIG. 8C          FIG. 8C-1

VARIABLE COMPRESSION SURGICAL FASTENER CARTRIDGE

CROSS-REFERENCE TO RELATED APPLICATIONS

This application claims priority to U.S. Provisional Application Ser. No. 61/044,652 filed Apr. 14, 2008, the entire contents of which is incorporated herein by reference in its entirety.

BACKGROUND

1. Technical Field

The present disclosure relates to surgical fastener applying apparatus. More particularly, the present disclosure relates to a surgical fastener applying apparatus that includes a plurality of surgical fasteners configured to apply varying compressive forces to tissue, and methods of using the same.

2. Background of the Related Art

Commercially available surgical fastening apparatus are well known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. U.S. Pat. Nos. 5,915,616, 6,202,914, 5,865,361, and 5,964,394 each describe one or more suitable apparatus which may be employed while performing one of these procedures.

In general, a surgical fastening apparatus will include an anvil that is approximated relative to a fastener cartridge during use or a fastener cartridge that is approximated relative to an anvil. The anvil includes depressions that are aligned with, and/or are in registration with slots defined in the cartridge, through which the fasteners will emerge, to effectuate formation. The fastener cartridge typically has one or more rows of fasteners disposed laterally or radially of a channel or knife slot that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners generally include a pair of legs adapted to penetrate tissue and connected by a backspan from which they extend. In use, subsequent to formation, the unitary fasteners have a "B" configuration. Typically, the two-part fastener includes legs that are barbed and connected by a backspan which are engaged and locked into a separate retainer piece that is usually located in the anvil. In use, the two-part fastener is pressed into the tissue so that the barbs penetrate the tissue and emerge from the other side where they are then locked into the retainer piece.

During each of the aforementioned surgical procedures, the tissue is initially gripped or clamped between the cartridge and anvil such that individual fasteners can be ejected from the cartridge, through the slots, and forced through the clamped tissue. Thereafter, the fasteners are formed by driving them into the depressions formed on the anvil.

A common concern in each of these procedures is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis, however, if too much pressure is applied, this can result in a needless reduction in blood flow to the tissue surrounding the cut-line. Accordingly, the joining of tissue together in this manner may result in an elevated level of necrosis, a slower rate of healing, and/or a greater convalescence.

Consequently, it would be advantageous to provide a surgical fastening apparatus capable of limiting the flow of blood in the tissue immediately adjacent the cut tissue to effectuate hemostasis and wound closure, while maximizing blood flow in the surrounding tissue to facilitate healing.

Additionally, when tissue is clamped and compressed between the anvil and cartridge, some of the fluid of the tissue is squeezed out so the tissue is compressed further at the center portions of the cartridge and anvil than at the lateral edges, thereby leaving thicker tissue at the edges. It would therefore be advantageous to provide staples which could better accommodate these resulting different tissue thicknesses.

SUMMARY

The present disclosure provides in one aspect a surgical fastener applying apparatus comprising a cartridge body including a tissue contacting surface including a plurality of fastener retention slots arranged in a plurality of rows including at least an inner row and an outer row, a plurality of surgical fasteners disposed in the inner and outer rows and configured such that a plurality of fasteners disposed in the inner row have a first diameter that is less than a second diameter of a plurality of surgical fasteners disposed in the outer row, and an anvil having an inner row and an outer row of depressions for forming the fasteners, a plurality of pushers are operably associated with the plurality of surgical fasteners, the pushers configured to eject the surgical fasteners towards the respective depression in the anvil such that upon formation of a corresponding surgical fastener, the plurality of surgical fasteners ejected from the inner row provide a greater compressive force to tissue than the plurality of surgical fasteners ejected from the outer row.

In one embodiment, the plurality of rows are spaced laterally on opposite sides of a channel that is located on the tissue contacting surface and configured to accommodate longitudinal movement of a knife operably associated with the cartridge body.

Preferably, the surgical fasteners include two legs extending from a backspan extending therebetween. In a preferred embodiment, when formed the surgical fasteners include a generally "B" shape wherein a tissue compression space of the plurality of formed surgical fasteners ejected from the inner row is less than a tissue compression space of the plurality of formed surgical fasteners ejected from the middle row.

In one embodiment, the two legs and the backspan include the same geometrical configuration such that the cross-sectional configuration of the surgical fastener is substantially uniform. In another embodiment, the two legs include the same geometrical configuration and the backspan includes a different geometrical configuration such that the cross-sectional configuration of the surgical fastener varies.

In one embodiment, the plurality of retention slots are arranged in a plurality of rows including at least an inner row, a middle row, and an outer row wherein the plurality of the fasteners disposed in the inner row have a diameter that is less than a diameter of the plurality of the surgical fasteners disposed in the middle row, and the surgical fasteners disposed in the middle row have a diameter that is less than a plurality of the surgical fasteners disposed in the outer row. In this embodiment, a tissue compression space of the plurality of formed surgical fasteners ejected from the inner row is less than a tissue compression space of the plurality of formed surgical fasteners ejected from the middle and outer rows.

In some embodiments, the cartridge body and anvil are pivotally attached. In other embodiments, at least one of the cartridge body and anvil is movable along a substantially linear path to move the cartridge and anvil into approximation.

The present disclosure provides in another aspect a surgical fastener cartridge for use with a surgical fastener applying apparatus comprising a cartridge body including a tissue contacting surface and having a plurality of fastener retention slots arranged in a first row and a second row, the first row being closer to a central longitudinal axis of the cartridge body than the second row, a plurality of surgical fasteners disposed in a first row and a second row, the first fastener row being closer to a central longitudinal axis of the cartridge body than the second fastener row, wherein least one of the fasteners disposed in the first fastener row has a diameter that is less than a diameter of at least one of the surgical fasteners disposed in the second fastener row.

Preferably, upon formation of the fasteners, a tissue compression space of the formed surgical fastener(s) ejected from the first row is less than a tissue compression spaced of the fastener(s) ejected from the second row.

The cartridge can include a longitudinal channel configured to accommodate longitudinal movement of a knife, wherein the plurality of rows are spaced laterally on opposite sides of the channel.

In a preferred embodiment, each of the surgical fasteners includes two legs connected by a backspan extending therebetween and when formed include a generally "B" shape. In some embodiments, the two legs and the backspan include the same geometrical configuration such that the cross-sectional configuration of the surgical fastener is substantially uniform. In other embodiments, the two legs include the same geometrical configuration and the backspan includes a different geometrical configuration such that the cross-sectional configuration of the surgical fastener varies.

The cartridge can include a third row of fasteners being positioned further from the central longitudinal axis than the second row, wherein a least one of the fasteners in the third row has a diameter greater than a diameter of the at least one fastener in the second row.

BRIEF DESCRIPTION OF THE DRAWINGS

Various embodiments of the present disclosure are described hereinbelow with references to the drawings, wherein:

FIG. 5A is a side perspective view of the surgical fastener configured for use with the cartridge depicted in FIG. 4 and having a first diameter and shown prior to formation;

FIG. 5A-1 is a side perspective cutaway view taken along line segment $A_1$-$A_1$ of the surgical fastener depicted in FIG. 5A;

FIGS. 6A-6D illustrate different surgical fasteners that include different backspan configurations in accordance with alternate embodiments of the present disclosure;

FIG. 7 is a side perspective view of the surgical fastener depicted in FIG. 5 shown subsequent to formation and within adjacent tissue segments;

FIGS. 8A-8C illustrate the surgical fastener depicted in FIG. 7 shown having three different diameters and being shown prior to and subsequent to formation (in phantom);

Figure 4:
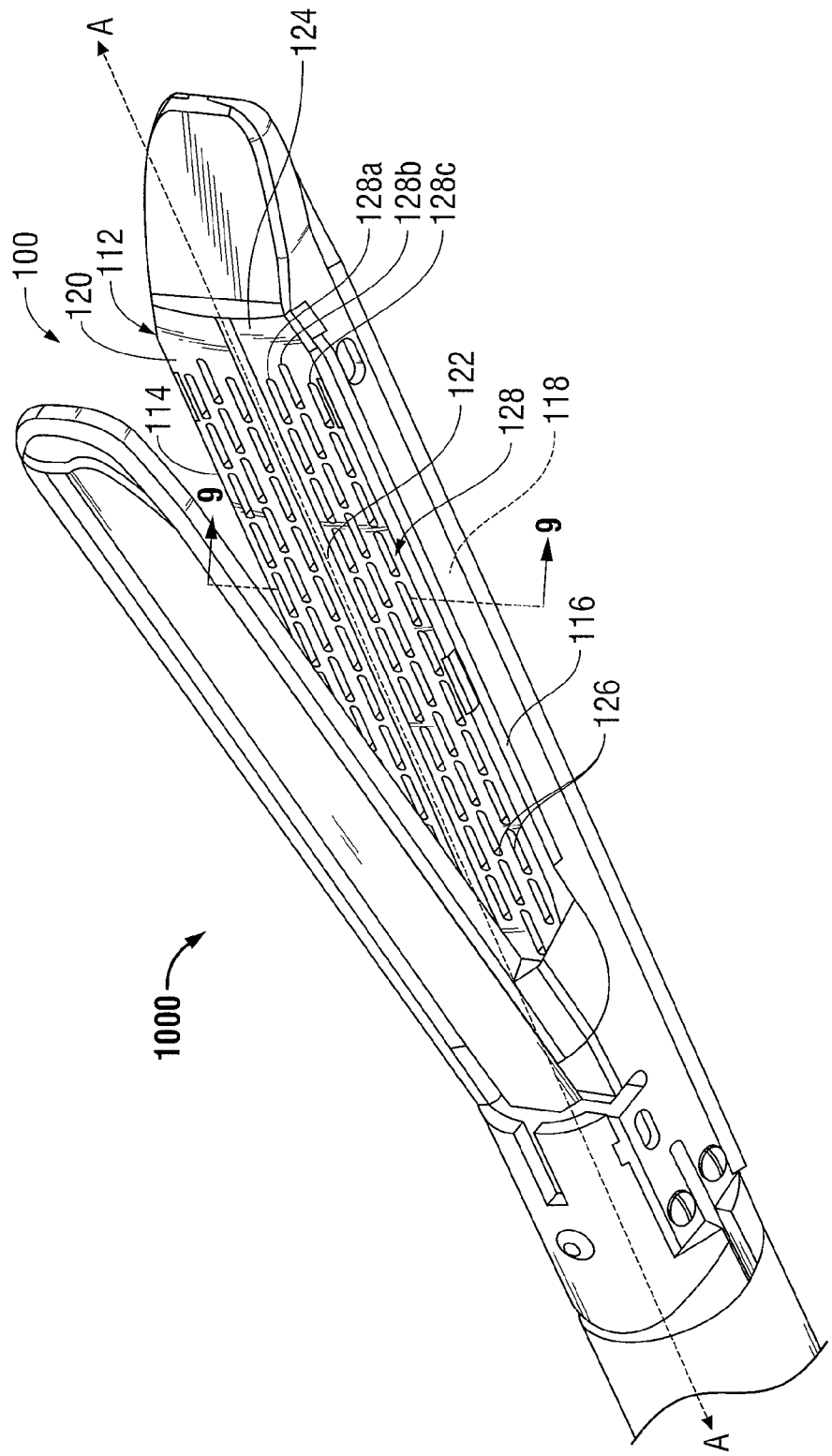
FIG. 4 is a top perspective view of a surgical fastener cartridge shown in the distal end portion of the surgical fastener device depicted in FIG. 1.
Figure 9:
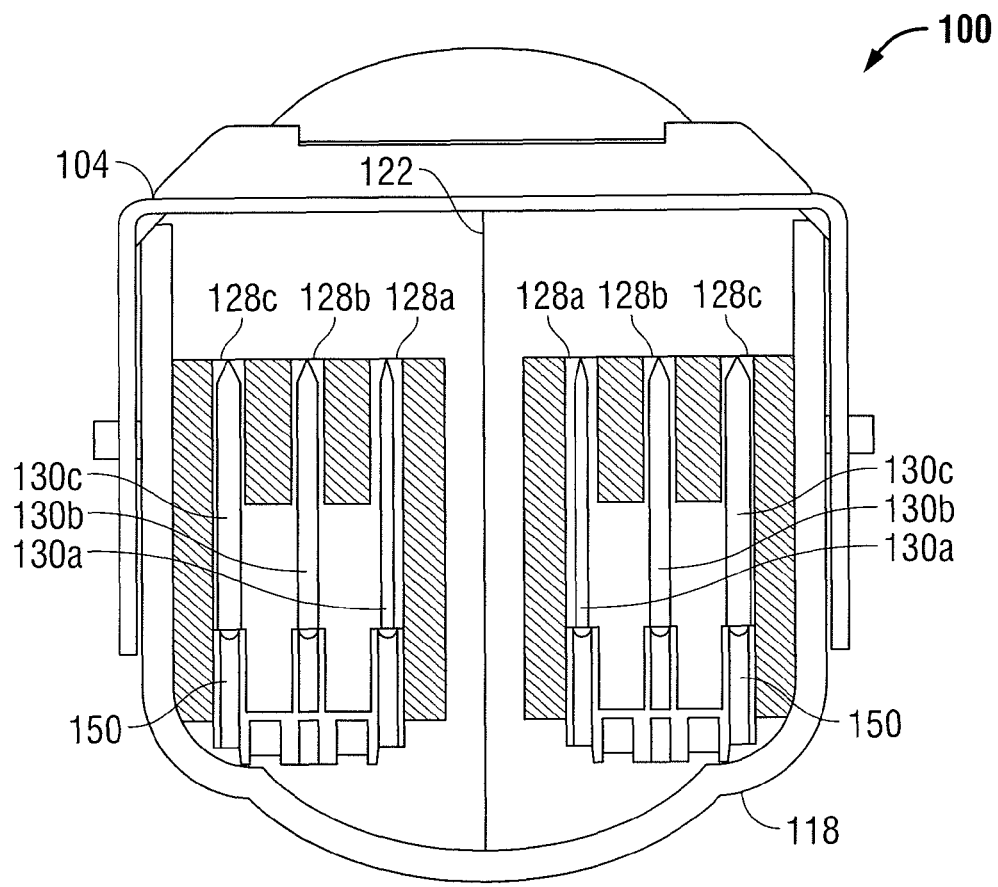
Figure 10:
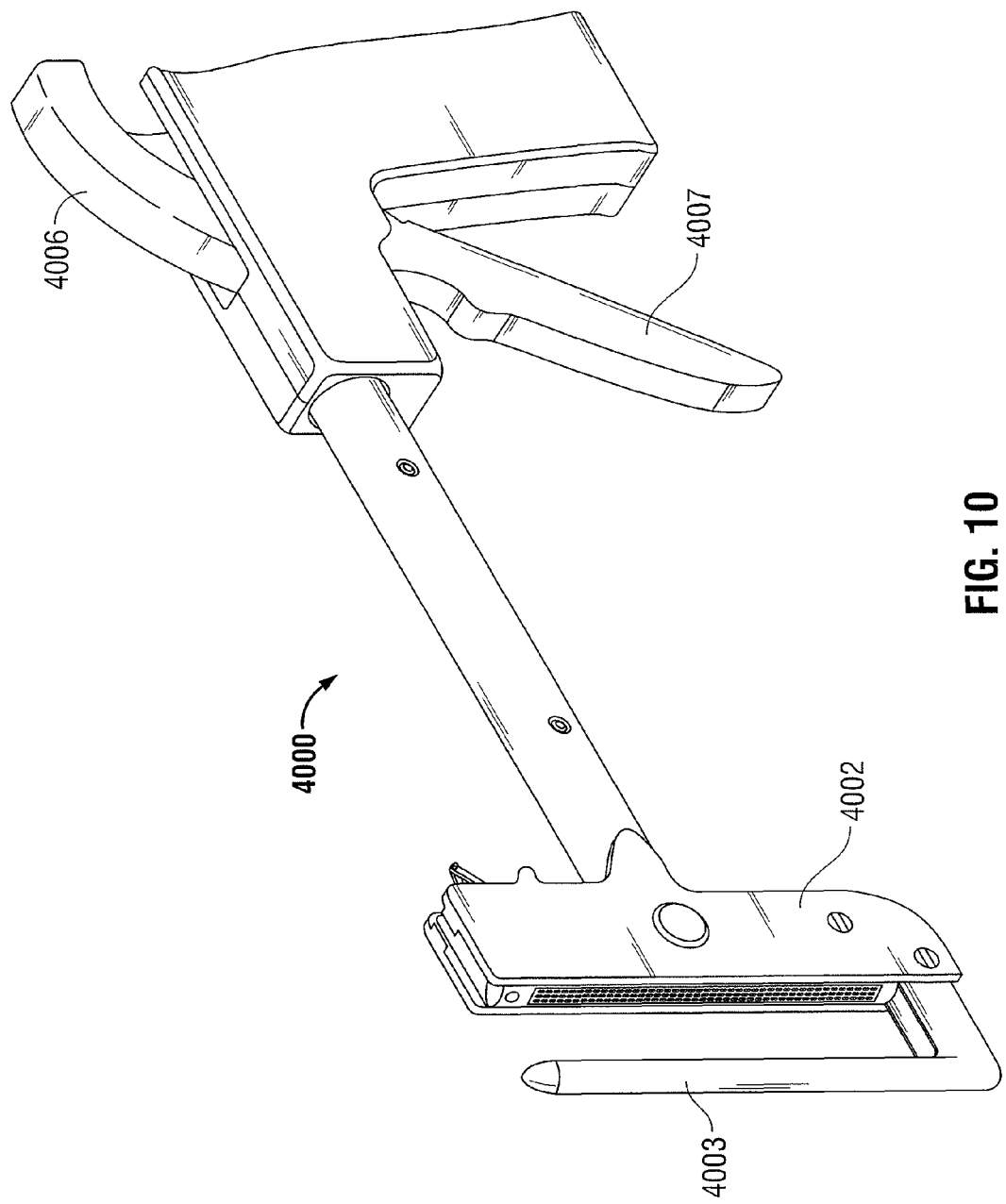

FIGS. $8A_{-1}$-$8C_{-1}$ illustrate side perspective cutaway views taken along line segments $A_1$-$A_1$ of the surgical fasteners depicted in FIGS. 8A-8C, respectively;

FIG. 9 is partial cross-sectional view taken along the line segment "9-9" in FIG. 4 illustrating the surgical fastener cartridge loaded with the surgical fasteners depicted in FIGS. 8A-8C; and FIG. 10 illustrates another type of surgical fastener device that may employ an alternate embodiment of surgical fastener cartridge in accordance with the present disclosure.

DETAILED DESCRIPTION OF EXEMPLARY EMBODIMENTS

Various exemplary embodiments of the presently disclosed surgical fastener cartridge, and method of manufacturing the same, will now be described in detail with reference to the drawings wherein like references numerals identify similar or identical elements. In the drawings and in the description which follows, the term "proximal" will refer to the end of the surgical fastener cartridge that is closer to the operator during use, while the term "distal" will refer to the end of the fastener cartridge that is further from the operator, as is traditional and conventional in the art. In addition, the term "surgical fastener" should be understood to include any substantially rigid structure formed of a biocompatible material that is suitable for the intended purpose of joining tissue together, including but not being limited to surgical staples, clips, and the like.

The present disclosure provides a surgical fastener cartridge adapted to house a plurality of surgical fasteners providing varying degrees of compression force to stapled tissue occupied therein such that an effective hemostatic effect at or near the cut-line may be achieved. To this end, the surgical fasteners are configured such that the surgical fasteners deployed closer to the cut line produce a greater compression force to stapled tissue than the surgical fasteners deployed further from the cut line.

Figure 1:
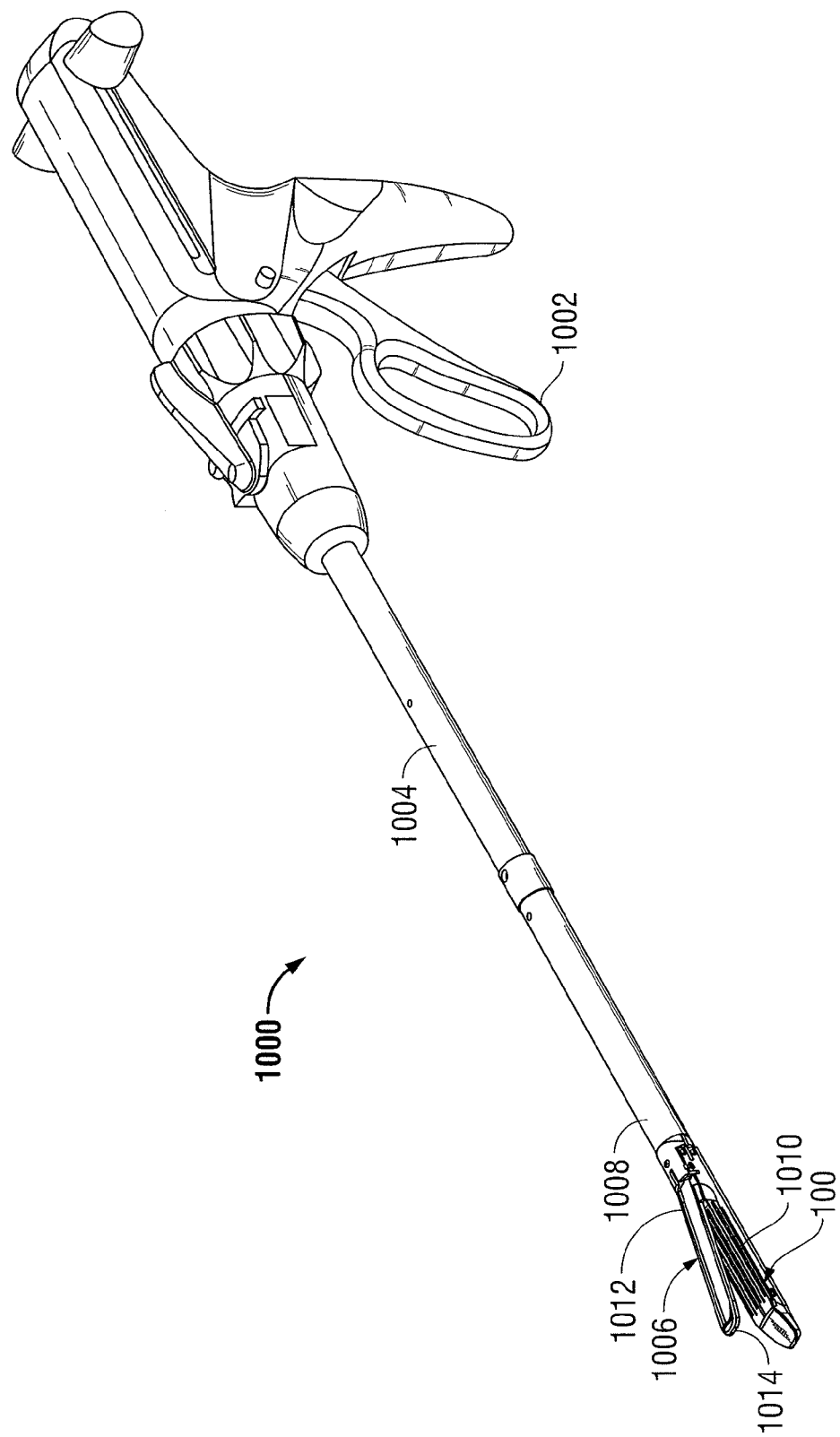
FIG. 1 illustrates an exemplary surgical fastener applying apparatus for use with a surgical fastener cartridge that employs surgical fasteners in accordance with embodiments of the present disclosure.

With reference to FIG. 1, a surgical fastener applying apparatus 1000 that employs a surgical fastener cartridge 100 is illustrated. Surgical fastener applying apparatus 1000 is used to sequentially apply a plurality of surgical fasteners to a patient's tissue. Surgical fastener apparatus 1000 may be configured for use, subsequent sterilization and reuse, or may be configured for single use. Surgical fastener applying apparatus 1000 includes a handle 1002, an elongated shaft or endoscopic portion 1004 extending distally therefrom, and an operative tool assembly 1006 coupled to a distal end 1008 of the elongated shaft 1004. In general, operative tool 1006 is adapted to clamp, sequentially fasten together, and sever adjacent tissue segments along a cut-line. Operative tool 1006 includes a pair of opposed jaws 1012, 1010 pivotally coupled to one another and respectively including an anvil member 1014 that is approximated relative to cartridge 100 during use. The anvil includes depressions that are aligned with, and/or are in registration with slots 126 defined in the cartridge 100, through which the fasteners 130 will emerge, to effectuate formation. For a more detailed discussion of the approximation and firing of surgical fastener applying apparatus 1000, reference is made to commonly owned U.S. Pat. No. 5,865, 361 currently assigned to Tyco Healthcare Group LP, the entire contents of which is incorporated herein by reference. In some embodiments, the cartridge and/or anvil is removable and replaceable.

Figure 2:
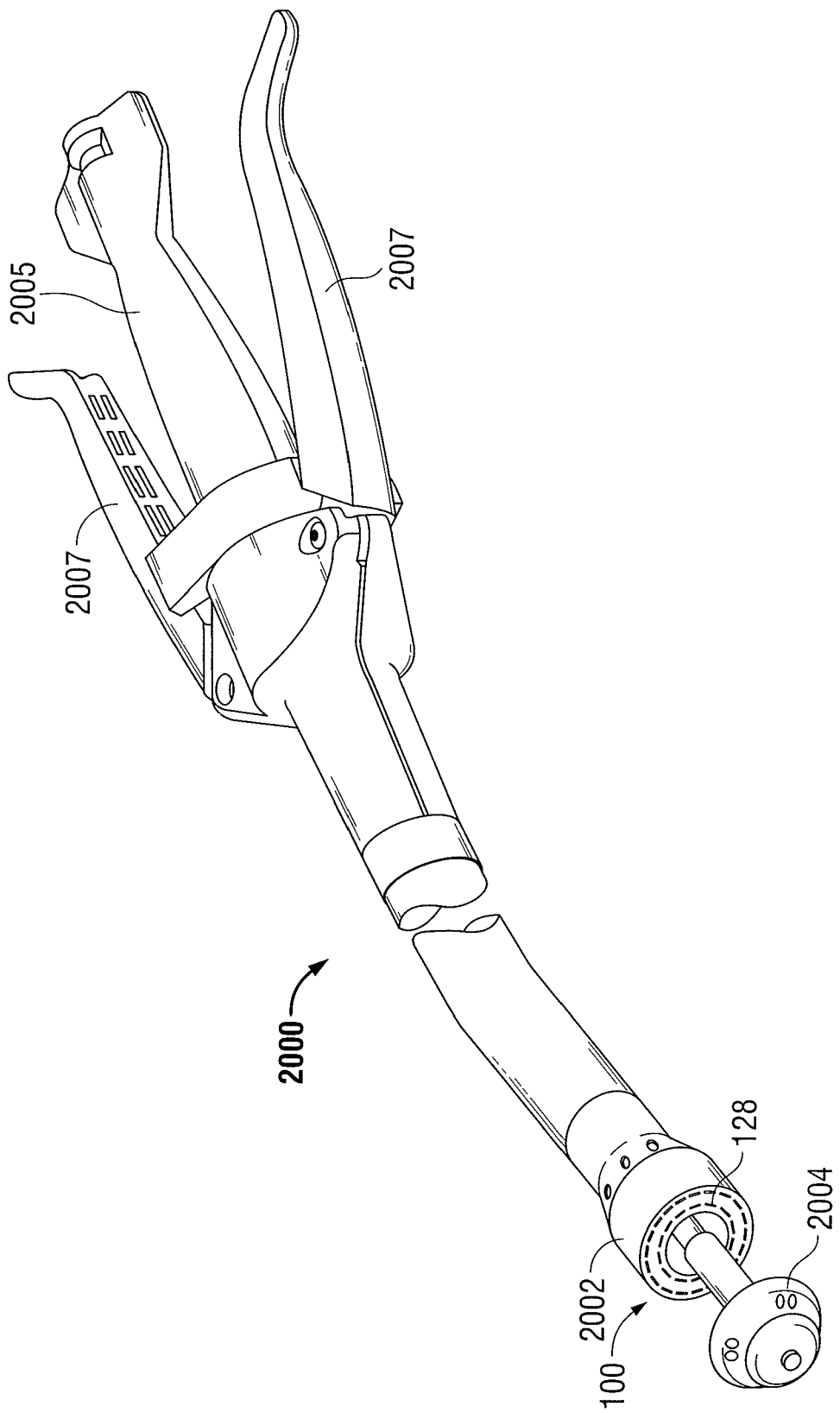
FIG. 2 illustrates another type of surgical fastener device that may employ an alternate embodiment of a surgical fastener cartridge in accordance with the present disclosure.
Figure 3:
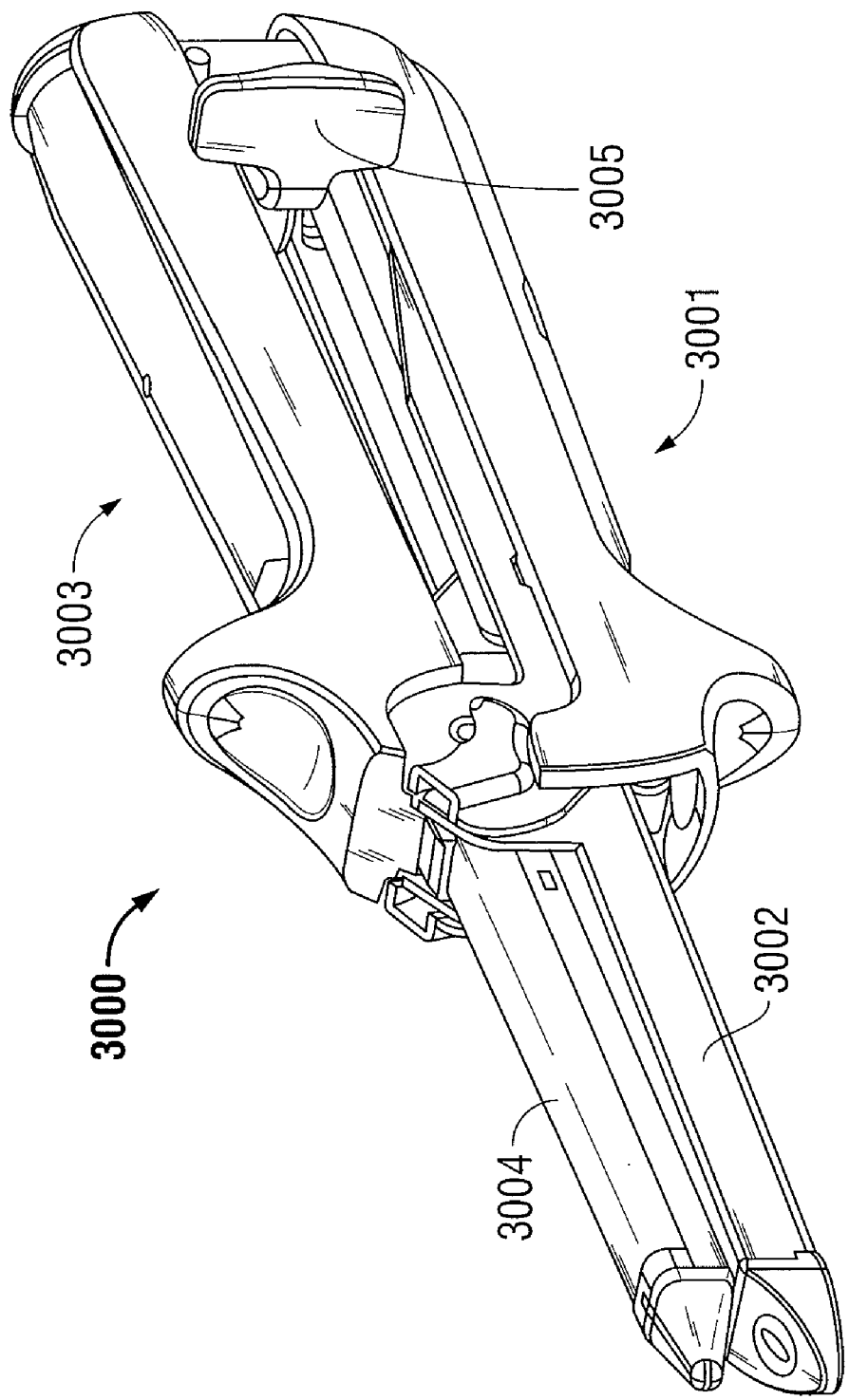
FIG. 3 illustrates another type of surgical fastener instrument that may employ an alternate embodiment of surgical fastener cartridge in accordance with the present disclosure.

While surgical fastener applying apparatus 1000 is depicted as an apparatus suitable for use in laparoscopic procedures for performing surgical anastomotic fastening of tissue, those skilled in the art will appreciate that cartridge 100 may be adapted for use with any surgical instrument suitable for the intended purposes described herein. For example, cartridge 100 may be adapted for use with an end-to-end anastomosis device 2000, as seen in FIG. 2, wherein the fasteners are arranged in substantially annular rows and/or a surgical stapling instrument 3000, as seen in FIG. 3, for use during an open gastro-intestinal anastomotic stapling procedure wherein the fasteners are arranged in substantially linear rows, or, for example, any of the surgical fastener applying apparatus disclosed in U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, which are each incorporated by reference herein in their entirety. The cartridge in some embodiments is removable and replaceable with another loaded cartridge.

For the purposes of brevity, the structural and operational features of cartridge 100 will be described in terms of use with the surgical fastener applying apparatus 1000.

With reference to FIG. 4, cartridge 100 of assembly 1006 is shown. Cartridge 100 extends along a longitudinal axis "A-A" and includes a cartridge body 112 with a pair of side walls 114, 116, a bottom wall 118, and a top wall 120. The top wall 120 includes a channel or knife slot 122 that is configured to accommodate longitudinal movement of a knife (not shown), or other suitable cutting element, such that stapled tissue may be severed along a cut-line. The top wall 120 further includes a tissue engaging surface 124 (e.g., for maintaining the position of the tissue to be cut) and a plurality of fastener retention slots 126 arranged into a plurality of rows 128 that extend substantially the length of the cartridge 100. As shown in FIG. 4, the fastener retention slots 126 are arranged into a pair of first (inner) rows $128_A$ that are spaced laterally from the knife slot 122 and on opposite sides thereof, a pair of second (middle) rows $128_B$ that are spaced laterally from the pair of first rows $128_A$ and on opposite sides of the knife slot 122, and a pair of third (outer) rows $128_C$ that are spaced laterally (outboard) from the pair of second rows $128_B$ and on opposite sides of knife slot 122. While the cartridge 100 is depicted as including pairs of first, second, and third rows $128_A$, $128_B$, $128_C$, respectively, it is within the purview of the present disclosure to have more or fewer rows of the fastener retention slots 126 (and fasteners) disposed on cartridge 100. Additionally, rows 128 may extend radially from the cutting element; such is the case when the fastening cartridge is employed with the surgical fastening device depicted in FIG. 2.

Each of the fastener retention slots 126 is configured to receive one of a plurality of surgical fasteners 130 and pushers 150 therein such that the surgical fasteners 130 are deployed in rows (e.g., inner, middle, and outer rows) on opposite sides of the cut-line created in the tissue during fastening, as shown in FIG. 9.

For a more detailed description of the functional and structural features of cartridge 100, reference is made to commonly owned U.S. Pat. No. 7,070,083 the entire contents of which are incorporated by reference herein.

With reference now to FIGS. 5A, $5_{A-1}$, and 6A-6D, cartridge 100 may loaded with one or more varieties of surgical fastener, represented generally as surgical fastener 130. Surgical fastener 130 of cartridge 100 is configured such that the surgical fastener 130 deployed closer to the cut line provides a greater compressive force to the stapled tissue than the surgical fastener 130 deployed further from the cut line. To this end, surgical fastener 130 includes two legs 132 extending from a backspan 134 extending therebetween. The thickness of the backspan 134 and the legs 132 can be varied such that the surgical fastener 130 closer to the cut line provides a greater compressive force to stapled tissue occupied therein than the surgical fastener 130 further from the cut line. The thickness of the backspan 134 and the legs 132 may also be varied to fasten adjacent tissue segments "$T_1$", "$T_2$" of varying thickness.

The legs 132 and the backspan 134 may define a cross-section having any suitable geometric configuration, including but not limited to rectangular, oval, square, triangular, and trapezoidal. The legs 132 and the backspan 134 may exhibit the same geometrical configuration such that the cross-sectional configuration of the surgical fastener 130 is substantially uniform, as shown in FIG. 5A, or, alternatively, the legs 132 and the backspan 134 may exhibit different geometrical configurations, e.g., the legs 132 may exhibit a rectangular cross-section and the backspan 34 may exhibit an oval cross-section, as shown for example in FIGS. 6A-6D, discussed in more detail below. Backspan 134 and/or legs 132 may be formed by any suitable means known in the art including but not limited to welding, braising, coining, casting, molding, overmolding and so on. Additionally, backspan 134 and/or legs 132 may be treated by way of annealing, cold working, heat treating, and so on. This may provide increased burst strength to the surgical fastener. Moreover, backspan may include different configurations of blocking and/or retainer material, tube, sleeve, collar, and/or grommet.

As seen in FIG. 5A, prior to the formation of surgical fastener 130, legs 132 extend from the backspan 134 such that they are substantially parallel. Alternatively, the legs 132 may converge or diverge from the backspan. The present disclosure contemplates that the surgical fastener 130 may also be configured as a directionally biased staple, such as those described in commonly owned U.S. Pat. No. 7,398,907, the entire contents of which are incorporated by reference herein.

Each of the legs 132 terminates in a penetrating end 136 that is configured to penetrate tissue (tissue segments "$T_1$", "$T_2$" for example) and/or other suitable material (blocking and/or retainer material for example). The penetrating ends 136 of legs 132 can be tapered to facilitate the penetration of tissue segments "$T_1$", "$T_2$", or alternatively, the penetrating ends 136 may not include a taper. In various embodiments, penetrating ends 136 may define a conical or flat surface, as described in co-pending U.S. patent application Ser. No. 11/444,761, filed Apr. 13, 2003, the entire contents of which are incorporated by reference herein. In some embodiments, one or both of legs 132 may be barbed. Having legs 132 configured in such a manner may facilitate maintaining the surgical fastener 130 in a fixed position within the tissue and/or blocking material.

Turning now to FIG. 7, surgical fastener 130 is shown subsequent to formation. Surgical fastener 130 is configured to provide a compression force to stapled tissue occupied therein. To this end, legs 132 cooperate with backspan 134 to maintain adjacent tissue segments "$T_1$", "$T_2$" in approximation and apply a compressive force "F" thereto. The compressive force "F" applies pressure to the tissue segments "$T_1$", "$T_2$", thereby restricting the flow of blood through the tissue surrounding the surgical fastener 130 and facilitating hemostasis. The linear configuration of the backspan 134 may limit the amount of pressure that can be applied to the tissue segments "$T_1$", "$T_2$" such that the flow of blood through the tissue is not completely restricted. When formed, the surgical fastener 130 has a generally "B" shape with an overall height "$H_F$" (measured from the outermost surface of the backspan 134 to the outermost curve of the legs 132) and a tissue compression space 140.

With reference to FIGS. 8A-8C, and FIGS. 8A-1-8C-1, respectively, surgical fastener 130 will be described in terms of surgical fasteners $130_A$, $130_B$, and $130_C$. Surgical fasteners $130_A$, $130_B$, and $130_C$ are respectively shown in their initial (unformed) and formed conditions (in phantom). Surgical fasteners $130_A$, $130_B$, $130_C$, are substantially similar to each other but for their respective diameters. The overall heights of the surgical fasteners $130_A$, $130_B$, $130_C$, in the unformed condition (measured from the penetrating tip of the legs to the outermost surface of the backspan) are shown as being substantially equal. The respective dimensions "$D_1$", "$D_2$", and/or "$D_3$" of surgical fasteners $130_A$, $130_B$ and $130_C$, may be altered, which, in turn, will alter the dimensions of the compression spaces $140_A$, $140_B$, $140_C$ occupied by stapled tissue segments "$T_1$", "$T_2$" when the respective surgical fasteners $130_A$, $130_B$, $130_C$ are in their formed conditions. One reason being, as the diameter of a surgical fastener increases so to does the driving force required to buckle them and form against the corresponding portion of the anvil. The driving force is provided by a pusher and sled configuration operatively connected to the cartridge 100. Because the pusher and sled are slightly flexible, they tend to "give" or deflect during formation of the surgical fasteners. Thus, surgical fasteners having larger diameters (e.g., surgical fasteners $130_B$ and/or $130_C$) will cause the pusher and sled to deflect more than surgical fasteners having smaller diameters (e.g., surgical fastener $130_A$). As a result, surgical fasteners having larger diameters form a "B" shape with a larger tissue compression space 140 and surgical fasteners having smaller diameters form a "B" shape with a smaller tissue compression space 140. By altering the respective dimensions of "$D_1$", "$D_2$", and/or "$D_3$" any desired level of hemostasis and blood flow in the stapled tissue segments "$T_1$", "$T_2$" may be effectuated. Other various attributes of the tissue (e.g., thickness or the presence of scar tissue) may increase or diminish the level of hemostasis and blood flow in the stapled tissue segments.

Surgical fastener $130_C$ has a diameter "$D_3$". When the surgical fastener $130_C$ is formed (phantomly shown in FIG. 8C) within tissue segments "$T_1$", "$T_2$", the backspan $134_C$ cooperates with the legs 132 of the surgical fastener $130_C$ to form tissue compression space $140_C$ (FIG. 8C). As noted, the surgical fasteners deployed further from the cut line tend to deflect the pusher and sled more than the surgical fasteners deployed closer to the cut-line, which, in turn, provides the largest compression zone. Compression space or zone $140_C$ provides minimal blood flow restriction when the tissue segments are stapled together.

Surgical fastener $130_B$ has a diameter "$D_2$", less than the diameter "$D_3$" of fastener $130_C$. When the surgical fastener $130_B$ is formed (phantomly shown in FIG. 8B) within tissue segments "$T_1$", "$T_2$", the backspan $134_B$ cooperates with the legs 132 of the surgical fastener $130_B$ to form tissue compression space $140_B$ (FIG. 8B). Here, because the diameter of surgical fastener $130_B$ is less than the diameter of surgical fastener $130_C$, the pusher and sled will deflect less than that as described above with regard to surgical fastener $130_C$. This results in formation of a tighter "B" shape with the resultant compression space $140_B$ less than the compression space $140_C$ of fastener $130_C$. Accordingly, because the pressure exerted on the tissue segments "$T_1$", "$T_2$" by surgical fastener $130_B$ is greater than the pressure exerted on the tissue segments "$T_1$", "$T_2$" by surgical fastener $130_C$, the blood flow through the tissue surrounding surgical fastener $130_B$ will be less (more restricted) than the blood flow through the tissue surrounding surgical fastener $130_C$, thereby further facilitating hemostasis. However, because blood flow is not completely restricted through tissue compression space $140_B$, unnecessary necrosis of the stapled tissue may be prevented and/or impeded.

Surgical fastener $130_A$ has a diameter "$D_1$", less than the diameter "$D_2$" of fastener $130_B$. When the surgical fastener $130_A$ is formed (phantomly shown in FIG. 8A) within tissue segments "$T_1$", "$T_2$", the backspan $134_A$ cooperates with the legs 132 of the surgical fastener $130_A$ to form tissue compression space $140_A$ (FIG. 8A). Here, because the diameter of surgical fastener $130_A$ is less than the diameters of surgical fasteners $130_B$ and $130_C$, the pusher and sled will deflect less than that as described above with regard to surgical fasteners $130_B$ and $130_C$. This results in formation of an even tighter "B" shape with the resultant compression space $140_A$ less than the compression space $140_B$ of fastener $130_B$. Accordingly, because the pressure exerted on the tissue segments "$T_1$", "$T_2$" by surgical fastener $130_A$ is greater than the pressure exerted on the tissue segments "$T_1$", "$T_2$" by surgical fasteners $130_B$, $130_C$, the blood flow through the tissue surrounding surgical fastener $130_A$ will be less (more restricted) than the blood flow through the tissue surrounding surgical fasteners $130_B$, $130_C$, thereby further facilitating hemostasis. Because blood flow is substantially, if not completely restricted through tissue compression space $140_A$, this results in facilitating and effectuating hemostasis.

FIG. 9 illustrates the surgical fasteners $130_A$, $130_B$, and $130_C$ loaded within the cartridge body 112 shown in FIGS. 1 and 4. The surgical fasteners $130_A$, $130_B$, and $130_C$ are arranged to define a pair of inner, middle, and outer rows $128_A$, $128_B$, and $128_C$, respectively, of fastener retention slots 126 formed in the top wall 120. The pair of inner, middle, and outer rows $128_A$, $128_B$, and $128_C$, respectively, are each spaced laterally from the knife slot 122, on opposite sides thereof, such that the surgical fasteners $130_A$, $130_B$, and $130_C$ will be deployed on opposite sides of the cut-line (not shown) created in the tissue upon fastening. That is, the fasteners $130_A$ with the smallest diameter provide a greater compressive force in the illustrated embodiment are provided in the inner rows closer to the cut line. The fasteners $130_B$, due to their larger diameter, are provided on the outer rows where the tissue might be thicker as a result of clamping by the instrument jaws (anvil and cartridge). If a third row of fasteners $130_C$ is used in this embodiment, then the fasteners of FIG. 8C with the largest diameter (largest compression space) would preferably be placed on the outermost row furthest from the cut line. It should be appreciated, however, that the fasteners can be placed on other rows than the foregoing. Also, while the inner, middle, and outer rows $128_A$, $128_B$, and $128_C$, respectively, are shown as including the surgical fasteners $130_A$, $130_B$, $130_C$, respectively, the present disclosure contemplates the inclusion of the surgical fasteners $130_A$, $130_B$, and 130$_C$, in other rows or arrangement of any of the surgical fasteners 130$_A$, 130$_B$, and 130$_C$, disclosed herein, either exclusively, such that only a single surgical fastener, e.g., surgical fastener 130, is present in a particular row, or in combination, such that a variety of surgical fasteners, e.g., surgical fasteners 130$_A$, 130$_B$, and 130$_C$, are present in one or more of the rows.

In one particular embodiment, the outer rows 128$_C$, intermediate rows 128$_B$, and inner rows 128$_A$ are comprised solely of surgical fasteners 130$_C$, 130$_B$, and 130$_A$, respectively such that the flow of blood through the tissue immediately surrounding the cut-line (not shown) is substantially, if not completely, restricted by the inner row 128$_A$ of surgical fasteners 130$_A$, whereas the flow of blood through the tissue surrounding the intermediate and outer rows 128$_B$, 128$_C$ is less restricted by surgical fasteners 130$_B$, 130$_C$, respectively. Accordingly, the flow of blood is minimized in the tissue immediately adjacent the cut-line and is increased gradually as the lateral distance from the cut-line is also increased. Also by this arrangement, the fasteners with the largest diameter (fasteners 130$_C$), are furthest from the cut line where the tissue is generally compressed to the lesser extent and the fasteners with the smaller diameter are positioned in the inner rows where the tissue is compressed to the greater extent. It should be appreciated that the diameters of the fasteners could be varied to accommodate tissue of different thicknesses and to control tissue compression by the fasteners.

In the embodiment of FIGS. 5 and 7, the backspan and legs are shown having a uniform diameter. It should be appreciated that the diameter of the legs and backspan, or portions thereof, can vary within the fastener. Examples of varying size backspan are shown in FIGS. 6A-6B. In the embodiment of FIG. 6A, the backspan is enlarged with respect to the legs and is an integral element 234 in which the fastener legs 232 are embedded. In FIG. 6C, the backspan is 334 is integral with the fastener legs 332. In the embodiments of FIGS. 6B and 6D, a separate backspan material is attached to the fastener 430, 530, respectively, with backspan 434 of FIG. 6B including a cylindrical collar 435 encircling the backspan portion 431 of the fastener 430 and the backspan 534 of fastener 530 of FIG. 6D encompassing the backspan portion 531 of the fastener and a portion of the fastener legs 532. The backspan material of FIGS. 6B and 6D can be composed of thermoplastic overmolded on the staple wire, by way of example. Varying the thickness or height of these backspans or backspan materials can vary the compression force of the formed staple by varying the distance between the curved legs and inner portion of the backspan. This variation can be provided in addition to the varying diameters of the fastener to accommodate varying tissue thicknesses. FIG. 6B illustrates this varying backspan by showing in phantom a collar of larger diameter (D2 compared to D1) to decrease the compression area. Other backspan shapes and attachments to achieve the various compression forces are also contemplated.

From the foregoing and with reference to the various figure drawings, those skilled in the art will appreciate that certain modifications can also be made to the present disclosure without departing from the scope of the same. For example, the surgical fasteners described herein above may be formed from a variety of surgically acceptable materials including titanium, plastics, bio-absorbable materials, etc. Additionally, any of the aforementioned surgical fasteners may be treated, chemically or otherwise, prior to being loaded into cartridge 100.

It is also contemplated that the backspan 134 of the surgical fastener 130 may include one or more pockets (not explicitly shown) that are positioned to engage the legs 132 during formation of the surgical fastener 130 and configured to redirect the legs 132 such that they are coiled toward the backspan 134, as discussed in commonly owned U.S. patent application Ser. No. 11/444,664, filed Jun. 1, 2006, the entire contents of which are incorporated by reference herein.

The surgical fastening cartridge 100 and anvil may also be employed with a surgical fastener applying apparatus 4000 (FIG. 10) that is used to simultaneously deploy a plurality of surgical fasteners, arranged in substantially linear rows transverse to a longitudinal axis of the apparatus, into either side of a target section of tissue (not explicitly shown). Here, a scalpel or other such cutting element may be used to remove the target section of tissue, or a built in knife could be provided which could be advanced upon advancement (firing) of the fasteners. The fasteners 130 would be supported within the cartridge or fastener supporting portion 4002. Approximation of the cartridge and anvil supporting portion 4003, e.g. linear movement of the fastener supporting portion 4002 toward the anvil supporting portion 4003, via movement of lever 4006 clamps tissue therebetween. The fasteners can then be advanced into the anvil pockets as described above upon squeezing of handle 4007, providing varying compressive forces on the tissue due to the varying diameters. Further details regarding the use and function of surgical fastener applying apparatus 4000 may be obtained through reference to U.S. Pat. Nos. 7,070,083 and 5,964,394 the entire contents of which are incorporated herein by reference. In an alternate embodiment, the apparatus 4000 could include a cutting element as in the other cartridges disclosed herein. Such staplers can also include other mechanisms for approximating the anvil and cartridge and firing the fasteners. The cartridge and anvil can also be used with other apparatus for simultaneously deploying a substantially linear row of fasteners, such as U.S. Pat. No. 7,407,076, the entire contents of which is incorporated herein by reference.

As noted above, the surgical fastening cartridge 100 may also be employed with a surgical fastener applying apparatus 3000 (FIG. 3) that is used to sequentially deploy a plurality of surgical fasteners arranged in substantially linear rows substantially aligned with the longitudinal axis of the apparatus, into either side of a target section of tissue (not explicitly shown). Here, a knife is advanced with the firing of the fasteners. The fasteners 130 would be supported within the cartridge or fastener supporting portion 3002. The instrument halves 3001 and 3003 are clamped together to approximate the cartridge and anvil, and movement of firing knob 3005 sequentially fires the fasteners into contact with the anvil pockets of the anvil portion 3004, providing varying compressive forces on the tissue due to the varying diameters.

As noted above, the surgical fastening cartridge 100 may also be employed with a surgical fastener applying apparatus 2000 (FIG. 2) that is used to simultaneously deploy a plurality of surgical fasteners arranged in substantially annular rows, into either side of a target section of tissue (not explicitly shown). Here, a knife is advanced with the firing of the fasteners. The fasteners 130 would be supported within the cartridge or fastener supporting portion 2002 Approximation of the cartridge 2002 and anvil 2004, e.g. retraction of the anvil 2004 by rotation of approximation knob (wing nut) 2005 clamps tissue between the anvil 2004 and cartridge 2002. The fasteners can then be advanced into the contact with the anvil pockets by squeezing of handles 2007, providing varying compressive forces on the tissue due to the varying diameters Although the illustrative embodiments of the present disclosure have been described herein with reference to the accompanying drawings, the above description, disclosure, and figures should not be construed as limiting, but merely as exemplary of various embodiments.

What is claimed is:

1. A surgical fastener applying apparatus comprising:
   a cartridge body including a tissue contacting surface, the tissue contacting surface including a plurality of fastener retention slots arranged in a plurality of rows including at least an inner row and an outer row;
   a plurality of surgical fasteners disposed in the inner and outer rows, and configured such that a plurality of fasteners disposed in the inner row have a first diameter that is less than a second diameter of a plurality of surgical fasteners disposed in the outer row;
   an anvil having an inner row and an outer row of depressions for forming the fasteners; and
   a plurality of pushers operably disposed within the cartridge body, each pusher of the plurality of pushers being operably associated with a respective one of the plurality of surgical fasteners to eject the surgical fasteners towards the respective depression in the anvil, the plurality of pushers are flexible to provide a requisite driving force to form the inner and outer rows of fasteners against the respective depressions in the anvil such that the plurality of surgical fasteners disposed in the outer row deflect the pushers more than the plurality of surgical fasteners disposed in the inner row such that upon formation of a corresponding surgical fastener, the surgical fasteners ejected from the inner row provide a greater compressive force to tissue than the surgical fasteners ejected from the outer row.

2. A surgical fastener applying apparatus according to claim 1, wherein the plurality of rows of fasteners are spaced laterally on opposite sides of a channel that is located on the tissue contacting surface and configured to accommodate longitudinal movement of a knife.

3. A surgical fastener applying apparatus according to claim 1, wherein the surgical fasteners includes two legs extending from a backspan extending therebetween.

4. A surgical fastener applying apparatus according to claim 3, wherein when formed the surgical fasteners include a generally "B" shape and a tissue compression space of the formed surgical fasteners ejected from the inner row is less than a tissue compression space of the formed surgical fasteners ejected from the outer row.

5. A surgical fastener applying apparatus according to claim 3, wherein the two legs and the backspan include the same geometrical configuration such that the cross-sectional configuration of the surgical fastener is substantially uniform.

6. A surgical fastener applying apparatus according to claim 3, wherein the two legs include the same geometrical configuration and the backspan includes a different geometrical configuration such that the cross-sectional configuration of the surgical fastener varies.

7. A surgical fastener applying apparatus according to claim 1, wherein the plurality of retention slots are arranged in a plurality of rows including at least an inner row, a middle row, and an outer row.

8. A surgical fastener applying apparatus according to claim 7, wherein the plurality of surgical fasteners are disposed in the inner, middle, and outer rows and configured such that the fasteners disposed in the inner row have a diameter that is less than a diameter of the surgical fasteners disposed in the middle row, and the surgical fasteners disposed in the middle row have a diameter that is less than the surgical fastener disposed in the outer row.

9. A surgical fastener applying apparatus according to claim 8, wherein a tissue compression space of the formed surgical fasteners ejected from the inner row is less than a tissue compression space of the formed surgical fasteners ejected from the middle and outer rows.

10. A surgical fastener applying apparatus according to claim 1, wherein the cartridge body and anvil are pivotally attached.

11. A surgical fastener applying apparatus according to claim 1, wherein at least one of the cartridge body and anvil is movable along a substantially linear path to move the cartridge body and anvil into approximation.

12. A surgical fastener cartridge for use with a surgical fastener applying apparatus, the cartridge comprising:
    a cartridge body including a tissue contacting surface and a plurality of fastener retention slots arranged in a first row and a second row, the first row being closer to a central longitudinal axis of the cartridge body than the second row;
    a plurality of surgical fasteners disposed in a first row and a second row, the first row being closer to a central longitudinal axis of the cartridge body than the second row, at least one of the fasteners disposed in the first row has a diameter that is less than a diameter of at least one of the surgical fasteners disposed in the second row; and
    a plurality of flexible pushers operably disposed within the cartridge body, each pusher of the plurality of pushers being operably associated with a respective one of the plurality of surgical fasteners to eject the plurality surgical fasteners towards respective depressions in an anvil of the surgical fastener applying apparatus, the plurality of flexible pushers providing a requisite driving force to form the inner and outer rows of fasteners against the respective depressions in the anvil such that during formation of corresponding surgical fasteners, the plurality of surgical fasteners disposed in the second row deflect the plurality of pushers more than the plurality of surgical fasteners disposed in the first row such that the surgical fasteners ejected from the first row provide a greater compressive force to tissue than the surgical fasteners ejected from the second row.

13. The surgical fastener cartridge according to claim 12, wherein upon formation of the fasteners, a tissue compression space of the formed surgical fastener ejected from the first row is less than a tissue compression spaced of the fastener ejected from the second row.

14. A surgical fastener cartridge according to claim 12, further comprising a longitudinal channel configured to accommodate longitudinal movement of a knife, wherein the plurality of rows are spaced laterally on opposite sides of the channel.

15. A surgical fastener cartridge according to claim 12, wherein each of surgical fasteners includes two legs connected by a backspan extending therebetween.

16. A surgical fastener cartridge according to claim 15, wherein when formed the surgical fasteners include a generally "B" shape.

17. A surgical fastener cartridge according to claim 12, wherein the two legs and the backspan include the same geometrical configuration such that the cross-sectional configuration of the surgical fastener is substantially uniform.

18. A surgical fastener cartridge according to claim 12, wherein the two legs include the same geometrical configuration and the backspan includes a different geometrical configuration such that the cross-sectional configuration of the surgical fastener is varies.

19. The surgical fastener cartridge of claim 12, further comprising a third row of fasteners positioned further from the central longitudinal axis than the second row, wherein a least one of the fasteners in the third row has a diameter greater than a diameter of the at least one fastener in the second row.

* * * * *